(12) United States Patent
Fujieda (10) Patent No.: US 6,547,392 B2
(45) Date of Patent: Apr. 15, 2003

(54) OPHTHALMIC APPARATUS

(75) Inventor: Masanao Fujieda, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 155 days.

(21) Appl. No.: 09/819,641

(22) Filed: Mar. 29, 2001

(65) Prior Publication Data

US 2001/0026350 A1 Oct. 4, 2001

(30) Foreign Application Priority Data

Mar. 30, 2000  (JP) ........................................ 2000-094739

(51) Int. Cl.⁷ ................................................. A61B 3/10
(52) U.S. Cl. ...................................................... 351/212
(58) Field of Search ................................. 351/205, 206, 351/210, 211, 212, 236, 237, 239, 242

(56) References Cited

U.S. PATENT DOCUMENTS

| | | |
|---|---|---|
| 5,500,697 A | 3/1996 | Fujieda |
| 5,841,511 A | 11/1998 | D'Souza et al. |
| 5,875,019 A * | 2/1999 | Villani ........................ 351/211 |
| 5,907,388 A | 5/1999 | Fujieda |
| 5,963,300 A * | 10/1999 | Horwitz ....................... 351/209 |
| 6,033,075 A | 3/2000 | Fujieda |

FOREIGN PATENT DOCUMENTS

| | | |
|---|---|---|
| EP | 0 811 352 A2 | 12/1997 |
| JP | 3-188826 | 8/1991 |
| JP | 8-103413 | 4/1996 |

* cited by examiner

*Primary Examiner*—George Manuel
(74) *Attorney, Agent, or Firm*—Finnegan, Henderson, Farabow, Garrett & Dunner, L.L.P.

(57) ABSTRACT

An ophthalmic apparatus comprising an input unit with which data on eye refractive power distribution of an eye to be examined at far vision, which is an unaccommodated state of the eye, and data on eye refractive power distribution of the eye at near vision, which is an accommodated state of the eye are inputted, a display, and a calculation and control unit which obtains data on distribution of difference between both the inputted data on distribution, so as to display at least one of the following data on the display: the data on the eye refractive power distribution at far vision; the data on the eye refractive power distribution at near vision; and the obtained data on the distribution of difference.

9 Claims, 5 Drawing Sheets

Far Vision (Unaccommodated State)

FIG. 7A

Near Vision (Accommodated State)

FIG. 7B

OPHTHALMIC APPARATUS

BACKGROUND OF THE INVENTION

1. Field of the Invention

The present invention relates to an ophthalmic apparatus for measuring and analyzing refractive power distribution of an eye to be examined.

2. Description of Related Art

There is an apparatus known for measuring time-varying change in accommodative power of an eye (crystalline lens) to be examined. This type of apparatus measures eye refractive power varying with a fixation target, a gaze object, placed at far is moved closer to the eye, or the fixation target placed at near is moved farther from the eye.

However, this type of apparatus only measures eye refractive power of limited portions along specific meridian directions. Therefore, it is not capable of furnishing accommodative change of the eye (the crystalline lens) in detail.

SUMMARY OF THE INVENTION

The present invention has been made in view of the above circumstances and has an object to overcome the above problems and to provide an ophthalmic apparatus capable of furnishing accommodative change of the eye in detail.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus comprises an input unit with which data on eye refractive power distribution of an eye to be examined at far vision, which is an unaccommodated state of the eye, and data on eye refractive power distribution of the eye at near vision, which is an accommodated state of the eye are inputted, a display, and a calculation and control unit which obtains data on distribution of difference between both the inputted data on distribution, so as to display at least one of the following data on the display: the data on the eye refractive power distribution at far vision; the data on the eye refractive power distribution at near vision; and the obtained data on the distribution of difference.

In another aspect of the present invention, an ophthalmic apparatus comprises a projecting optical system for projecting a measurement target on a fundus of an eye to be examined, a detecting optical system for detecting an image of the measurement target formed on the fundus, a target presenting optical system for presenting a target to the eye at a variable distance, a display, a and calculation and control unit which obtains data on eye refractive power distribution over each portion of a cornea of the eye based on results detected by the detecting optical system, and further obtaining data on distribution of difference between the data on eye refractive power distribution that have been obtained with the target presented at different distances, so as to display at least the obtained data on the distribution of difference.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1A:
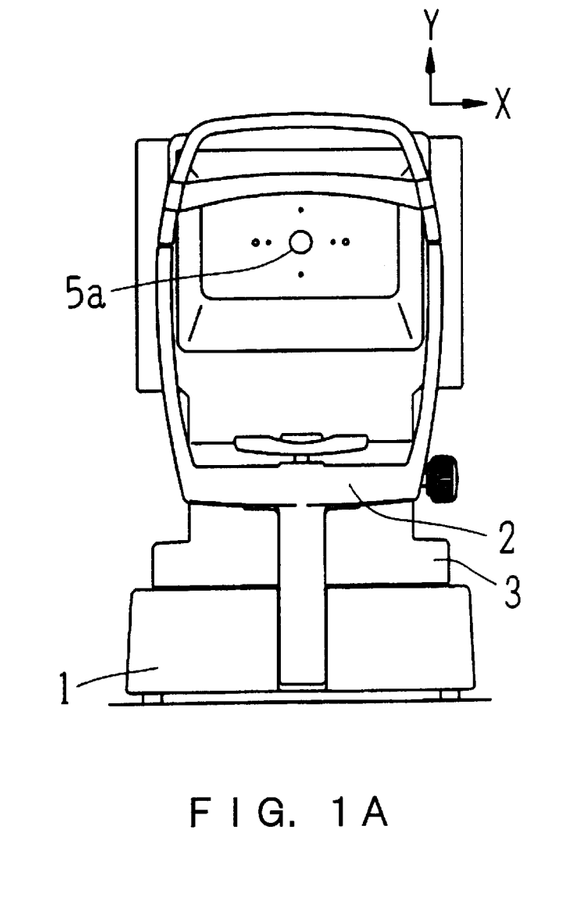
FIGS. 1A and 1B are external views showing construction of an ophthalmic apparatus in accordance with one preferred embodiment of the present invention.
Figure 1B:
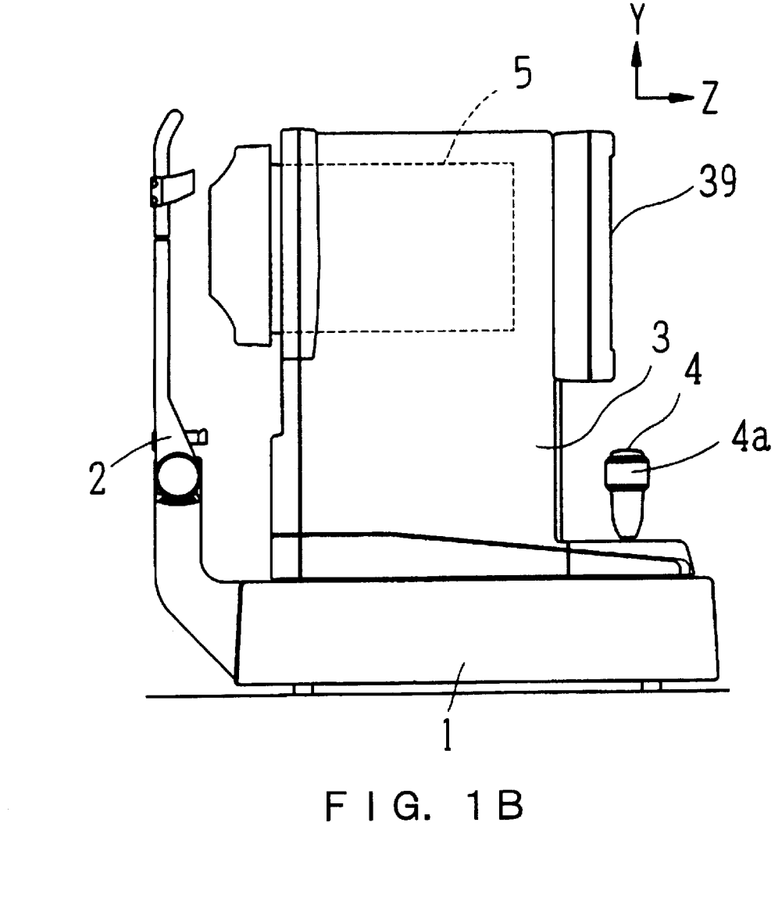
Figure 2:
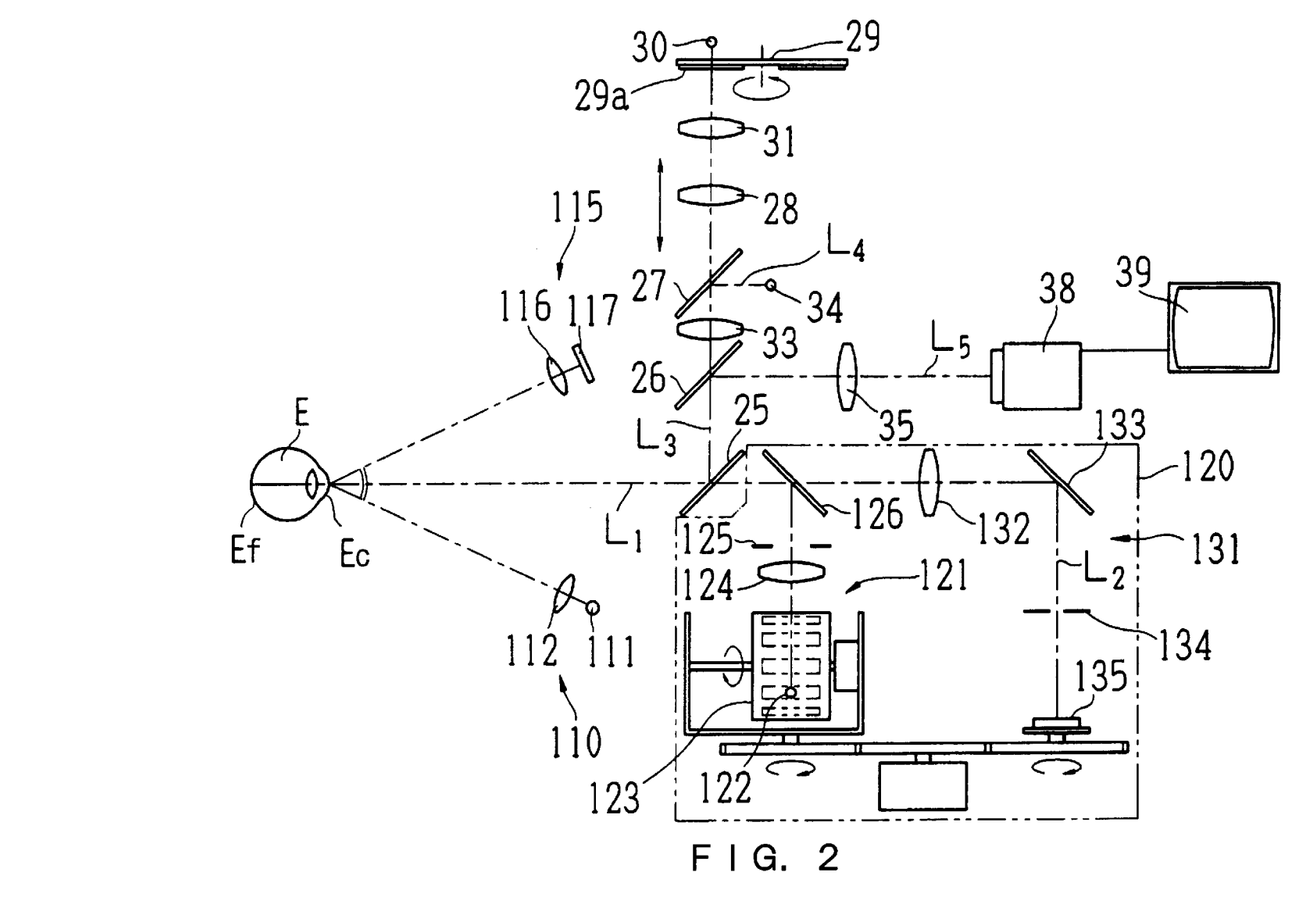
FIG. 2 is a schematic view showing construction of optical systems arranged inside a measurement unit of the apparatus.
Figure 3:
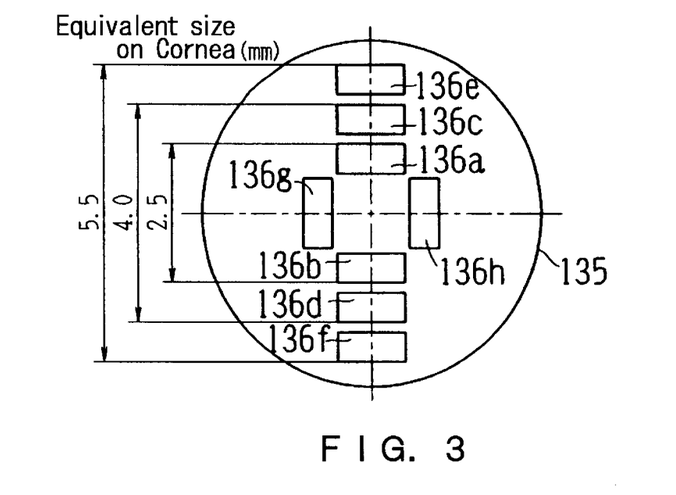
FIG. 3 is a schematic block diagram showing a control system of the apparatus.

A detailed description of one preferred embodiment of an ophthalmic apparatus embodying the present invention will now be given ref erring to the accompanying drawings. FIGS. 1A and 1B are external views showing construction of the apparatus in accordance with the preferred embodiment of the present invention: FIG. 1A is a front view, looking from an examinee's side and FIG. 1B is a side view. FIG. 2 is a schematic view showing construction of optical systems arranged inside a measurement unit 5. FIG. 3 is a schematic block diagram showing a control system of the apparatus.

Reference numeral 1 denotes a fixed base. The base 1 has a head support unit 2 fixedly attached thereto for fixedly supporting an examinee's head. 5 is the measurement unit containing a measurement optical system, an alignment optical system and the like, which will be described later. The measurement unit 5 is provided with a measurement window 5a on a side facing to the examinee at an approximate center in the right-and-left direction (X direction) so that measurement light and the like can pass through. A main body 3 on which the measurement unit 5 is mounted slides along the base 1 in the right-and-left direction (X direction) and the back-and-forth direction (Z direction) by a known slide mechanism which works in response to operation of a joystick 4. In addition, the measurement unit 5 moves in the up-and-down direction (Y direction) relative to the main body 3 by a Y direction movement device comprising a motor and the like, which is driven via a calculation and control unit 50 in response to rotative operation of a rotation knob 4a mounted at the joystick 4. Further, to be ready for auto-alignment, the measurement unit 5 may be moved in the X, Y and Z directions relative to the main body 3 by the calculation and control unit 50 as well as an X direction movement device, the Y direction movement device and a Z direction movement device, each of which comprises a motor and the like.

Reference numeral 39 is a color monitor (display) for displaying various information to the examiner, such as an image of an eye to be examined, alignment information, measurement results and the like.

In FIG. 2, an eye refractive power measurement optical system 120 is disposed behind a beam splitter 25 arranged on an optical axis L1. The eye refractive power measurement optical system 120 comprises a slit light projecting optical system 121 and a slit image detecting optical system 131. Near infrared light emitted from a light source 122 included in the slit light projecting optical system 121 illuminates slit apertures provided to a rotation sector 123. The slit light scanned by rotation of the sector 123 passes through a projecting lens 124 and a limiting diaphragm 125, then is reflected by a beam splitter 126. Thereafter, the light passes through the beam splitter 25, then converges in a vicinity of a cornea Ec of an eye E to be examined, and is projected onto a fundus Ef of the eye E.

The slit image detecting optical system 131 comprises a photo-receiving lens 132 and a mirror 133 both of which are disposed on an optical axis L1, as well as a diaphragm 134 and a photo-receiving unit 135 both of which are disposed on an optical axis L2 of light reflected by the mirror 133. The diaphragm 134 is arranged at a back focal point of the photo-receiving lens 132. The photo-receiving unit 135 has eight photo-detectors 136a–136h on its photo-receiving plane at generally conjugate positions with the cornea Ec relative to the photo-receiving lens 132 (see FIG. 4). Among the eight photo-detectors, the photo-detectors 136a–136f are located along a line passing though the center of the photo-receiving plane (the optical axis L2) such that the photo-detectors 136a and 136b, 136c and 136d, and 136e and 136f are symmetrical in relation to the center of the photo-receiving plane. These three pairs of photo-detectors are disposed at specific distances so as to be able to detect the refractive power at each corresponding position in the meridian direction on the cornea Ec (In FIG. 3, the distances are shown in the equivalent size on the cornea Ec). On the other hand, the photo-detectors 136g and 136h are disposed on a line orthogonal to the photo-detectors 136a–136f to be symmetrical in relation to the optical axis L2.

This eye refractive power measurement optical system 120 is so configured that a rotation mechanism comprising a motor, a gear and the like rotates the sector 123 and the photo-receiving unit 135 respectively on their optical axes in synchronism.

Disposed on an optical axis L3, which is made coaxial with the optical axis L1 by the beam splitter 25 are a half mirror 26, a lens 33, a half mirror 27, lenses 28 and 31, a fixation target 29a, and an illumination light source 30 such as an LED which emits visible light. As the fixation target 29a, there are provided a plurality of targets such as a landscape chart. as well as a visual acuity testing optotype of the Landolt ring type and the like. By rotating a target plate 29, the target placed on the optical axis L3 is switched to an intended type. The lens 28 is movable along the optical axis L3 so that the position of the fixation target 29a that the eye E gazes at is changed. This enables fogging the eye E upon eye refractive power measurement, or to apply accommodative load to the eye E upon eye refractive power measurement.

Disposed on an optical axis L4, which is made coaxial with the optical axis L3 by the half mirror 27 is a light source 34 such as an LED which emits near infrared light. Light emitted from the light source 34 is reflected by the half mirror 27, and then made generally parallel light by the lens 33 and projected onto the cornea Ec from the front via the half mirror 26 and the beam splitter 25. As a result, the light source 34 forms an image of an alignment target on the cornea Ec. Light of the target image formed on the cornea Ec enters a CCD camera 38 via the beam splitter 25, the half mirror 26 and a lens 35.

Disposed on an optical axis L5, which is made coaxial with the optical axis L3 by the half mirror 26 are the lens 35 and the CCD camera 38 serving as a photographic element. Output from the camera 38 is inputted into the monitor 39 directly or via the calculation and control unit 50. An image of an anterior eye segment of the eye E photographed by the camera 38 is displayed on the monitor 39. Also, the target image by the light source 34 is subjected to image processing performed by the calculation and control unit 50, thereby to obtain the alignment condition of the apparatus with the eye E in the up-and-down and the right-and-left directions (X and Y directions).

Reference numeral 110 is a target projecting optical system for working distance detection, and comprises a light source 111, such as an LED which emits near infrared light, and a lens 112. 115 is a target detecting optical system for working distance detection, and comprises a lens 116 and a one-dimensional photo-detector (a position-detector) 117. Light emitted from the light source 111 is made generally parallel light by the lens 112 and illuminates the cornea Ec obliquely. As a result, the light source 111 forms a target image on the cornea Ec. Light of the target image formed on the cornea Ec enters the detector 117 via the lens 116. Based on the incident position of the light on the detector 117, the calculation and control unit 50 detects an alignment condition of the apparatus with the eye E in a working distance direction (Z direction).

Now, description is given to operation of the apparatus. First, a measurement is performed in a mode for measuring eye refractive power at far vision where accommodation of the eye is relaxed (hereinafter, this mode is referred to as a far vision mode). This far vision mode is selected with a mode changeover switch 40. While observing an image of the anterior segment of the eye E illuminated by a not-illustrated illumination light source and displayed on the monitor 39, the examiner operates the joystick 4 and the like to align the apparatus (the measurement unit 5) with the eye E. To make alignment in the X and Y directions, an image of the alignment target, which is formed by the light source 34 at an optical center determined depending on the corneal optical system of the eye E (hereinafter, it is regarded to be the corneal center, which may be regarded also as an approximate center of the visual axis) is brought to the center of an aiming mark displayed on the monitor 39. This aiming mark may be generated electrically and its center is preliminarily adjusted to coincide with the photographing optical axis L5 of the camera 38 (the measurement optical axis L1). To make alignment in the Z direction, the calculation and control unit 50 displays an indicator for alignment on the monitor 39 based on information obtained by the detector 117 about deviation in the working distance direction. Then, the examiner moves the main body 3 in the Z direction according to the indicator.

Figure 4:
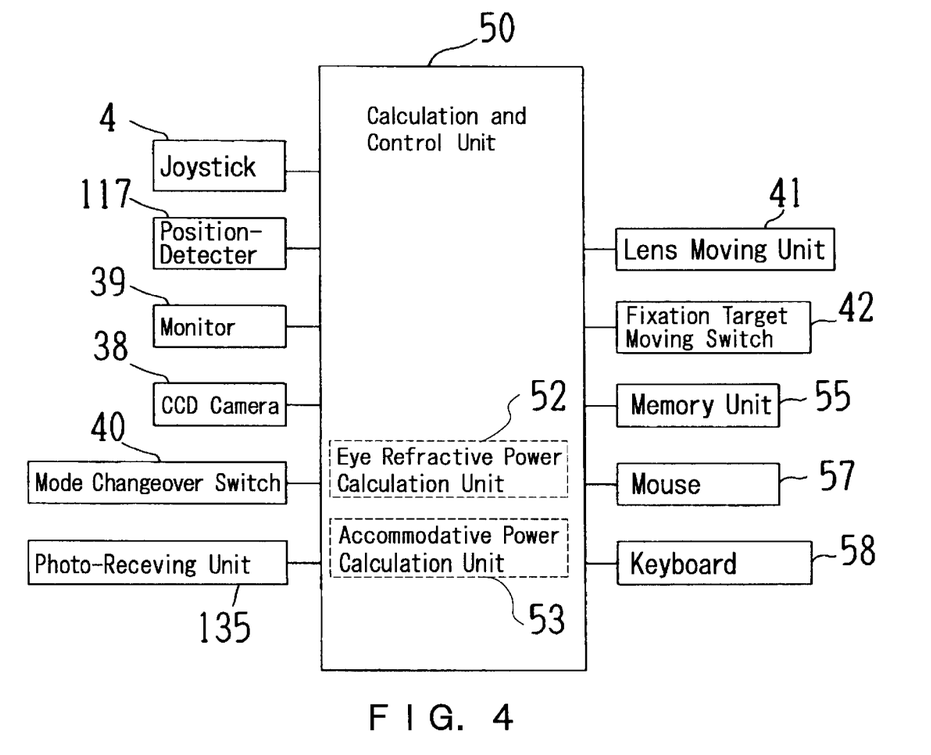
FIG. 4 is a view showing an arrangement of photodetectors included in a photo-receiving unit of an eye refractive power measurement optical system.

After the alignment is done, the examiner pushes a not-illustrated measurement switch to perform an eye refractive power measurement. An eye refractive power calculation unit 52 obtains the eye refractive power distribution based on the phase difference of the output signals from each photo-detector disposed in the photo-receiving unit 135. To meet this end, first, preliminary measurement is performed in the like manner as a conventional phase difference method to obtain refractive power. Based on the thus obtained result, the lens 28 is moved so as to place the fixation target 29a at a position approximately conjugate with the fundus Ef of the eye E, then the lens 28 is further moved in order to perform fogging for suitable diopters. The lens 28 is moved by a lens moving unit 41 comprising a motor and the like. Thereafter, based on the output signals from the photo-detectors 136g and 136h that vary in response to the movement of the slit image on the photo-receiving unit 135, the eye refractive power calculation unit 52 obtains the corneal center (or the center of the visual axis) in the meridian direction in which the photo-detectors 136a–136f are disposed. Next, based on the phase difference of the output signals from each of the photo-detectors 136a–136f with respect to the thus obtained center, refractive power at a plurality of corneal portions corresponding to each photo-detector is obtained. While rotating the sector 123 of the projecting optical system 121 and the photo-receiving unit 135 one hundred eighty degrees at a predetermined angle step (1 degree) about the optical axes, refractive power for each meridian at every angle step is calculated and stored one by one. As a result, the eye refractive power distribution which varies in the meridian direction is obtained (for the details, see U.S. Pat. No. 5,907,338).

Figure 5:
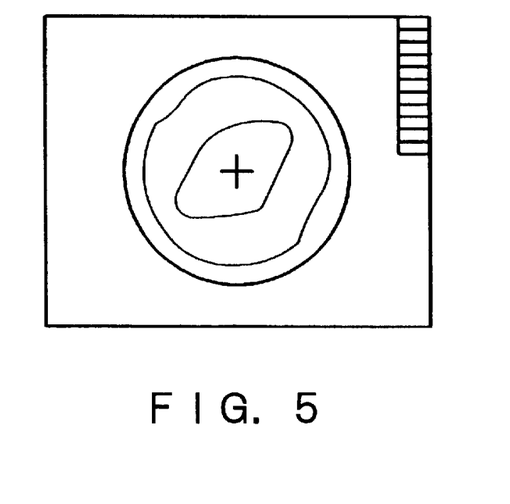
FIG. 5 is a view showing an example of display of results obtained through eye refractive power distribution measurement.

The thus obtained data on the eye refractive power distribution at far vision is stored in a memory unit 55 such as a hard disk or the like. In addition, as shown in FIG. 5, the eye refractive power distribution at far vision is graphically displayed on the monitor 39 in a color map format. The map is color-coded in accordance with predetermined steps of refractive power so that the change in the eye refractive power distribution is displayed in a color information format, which is perceived easily and visually.

Next, the mode changeover switch 40 is depressed so that a measurement is performed in a mode for measuring eye refractive power at near vision where the eye accommodative load is applied to the eye (hereinafter, this mode is referred to as a near vision mode). In the near vision mode, the fixation target 29a is moved to an intended near point by operating a fixation target moving switch 42. In response to a signal inputted from the switch 42, the calculation and control unit 50 drives the lens moving unit 41 to move the lens 28 so that the fixation target 29a is placed at an intended near point optically. For example, if the previously measured SE value (spherical equivalent value) of the eye refractive power at far vision is −3D (diopters), the lens 28 needs to be moved in such a manner to place the fixation target 29a at −3D−2.5D=−5.5D that corresponds to a near vision of 40 cm.

By fixating the eye E to the fixation target 29a that has been moved to a near point as above, accommodative load is applied to the eye E. The measurement switch is depressed under this condition to measure eye refractive power distribution at near vision. Similarly to the far vision measurement, the calculation unit 52 obtains eye refractive power distribution based on the phase difference of output signals from each photo-detector that the photo-receiving unit 135 comprises. The thus obtained data on the eye refractive power distribution at near vision is stored in the memory unit 55, and the eye refractive power distribution at near vision is graphically displayed on the monitor 39 in a color map format.

Once the data on the eye refractive power distribution at far vision and the data on the eye refractive power distribution at near vision are obtained in the above manner, the keyboard 58 and the mouse 57 which are connected to the calculation and control unit 50 are operated following the instructions displayed on the monitor 39. Through the operations, each data on distribution is inputted to an accommodative power calculation unit 53 so that eye refractive power distribution of the difference between both the distribution data (in this specification, this is referred to as accommodative power distribution) is calculated. That is to say, change in accommodation of the crystalline lens which occurs in response to the change in the accommodative load applied to the eye is obtained as two-dimensional distribution. The thus obtained data is stored in the memory unit 55 and displayed on the monitor 39.

Figure 6:
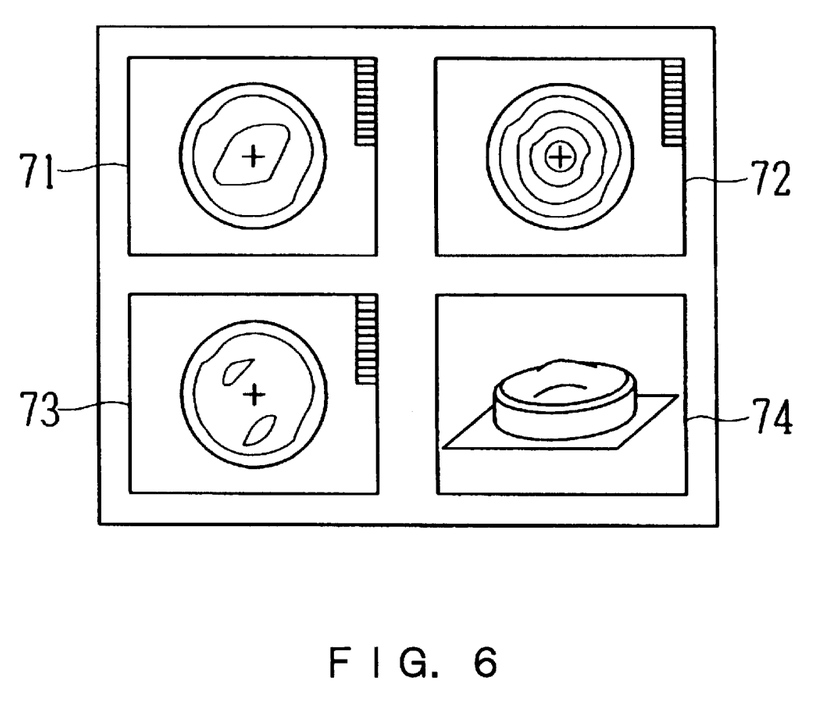
FIG. 6 is a view showing examples of display of eye refractive power distribution at far vision and near vision as well as accommodative power distribution.

FIG. 6 shows examples of display showing the results calculated by the accommodative power calculation unit 53 and the like. The monitor 39 displays the following four windows tiled on one screen: a color map 71 showing the eye refractive power distribution at far vision; a color map 72 showing the eye refractive power distribution at near vision; a color map 73 showing the accommodative power distribution which is the difference between the two distributions; and a three-dimensional display 74 with its vertical axis indicating the difference of the refractive power.

In addition, it is possible to calculate the minimum and maximum values in the accommodative power distribution, the average value for the overall measurement area, and the volume of the three-dimensional display 74 with the vertical axis indicating the difference of the refractive power. Then, the calculated data may be displayed on the monitor 39 as quantitative numeric data and stored in the memory unit 55.

Further, eye refractive power distribution at far vision and at near vision may be decomposed into aberration components using the Zernike polynomial expression. In this way, it is possible to find out which order aberration components have gone through increase or decrease. That is to say, in view of aberrations before and after the change in the crystalline lens, optical characteristics of a living eye can be known.

Figure 7A:
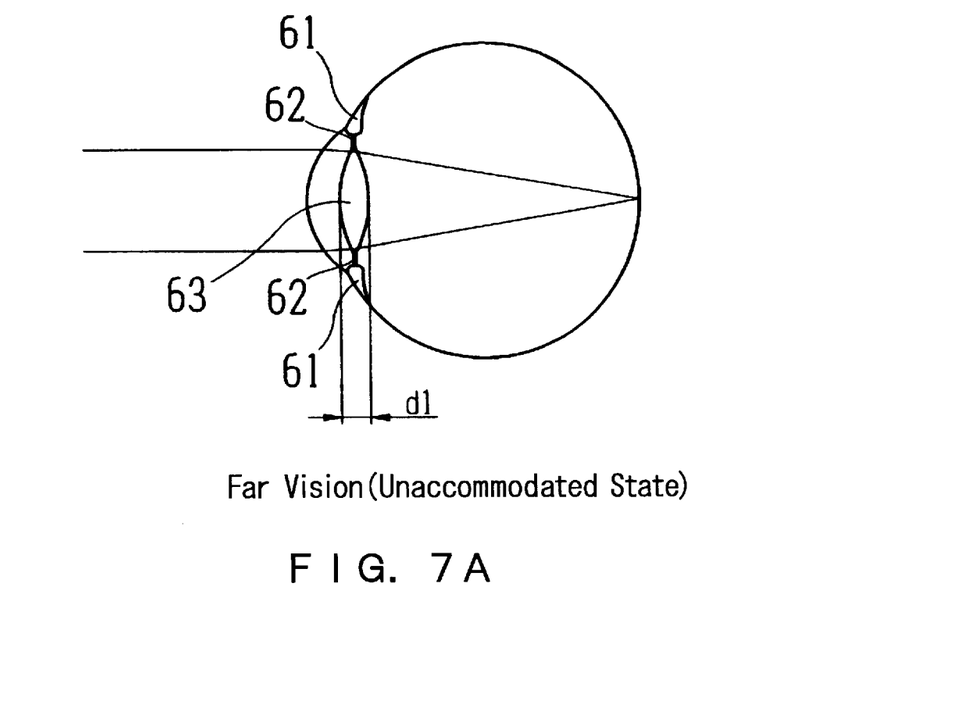
FIGS. 7A and 7B are views illustrating functions of a crystalline lens.
Figure 7B:
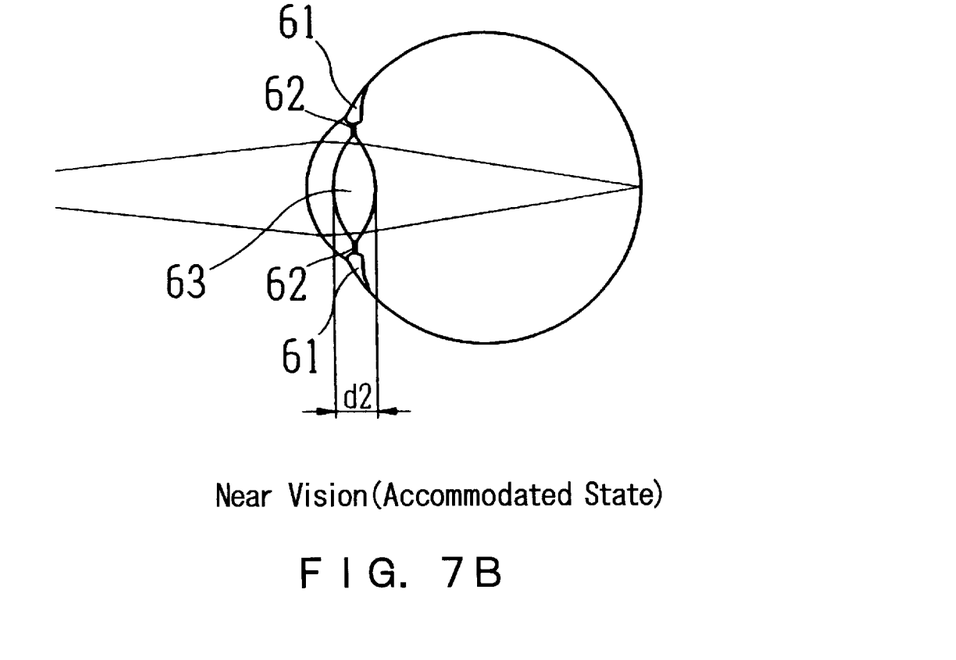

Here, operation of the crystalline lens of the eye is explained briefly. To see objects at various distances, if the eye is normal, the ciliary muscle operates to change the thickness of the crystalline lens to increase or decrease its refractive power, which brings an image of an object to be focused on the retina. As shown in FIG. 7A, at far vision (the state where the accommodation is relaxed), the ciliary muscle 61 is relaxed and, therefore the Zinn's zonules 62 vertically supporting the crystalline lens 63 are brought under tension, thereby pulling the crystalline lens 63. As a result, the thickness d1 of the crystalline lens 63 decreases and thus the refractive power decreases. On the contrary, as shown in FIG. 7B, at near vision (the accommodated state), the ciliary muscle 61 contracts and, therefore the Zinn's zonules 62 vertically supporting the crystalline lens 63 relax. As a result, the thickness d2 of the crystalline lens 63 increases owing to its own elasticity and thus greater refractive power is attained.

That is to say, it is helpful to calculate difference in the eye refractive power distribution when the accommodative load applied to the eye is varied, and further to graphically display it as the color map 73 in FIG. 6, or to display quantitative numeric data as described above. In this way, it is possible to provide information furnishing details on the operational mechanism of the crystalline lens and the accommodative state of the crystalline lens.

The data on the eye refractive power distribution at near vision and the data on the eye refractive power at far vision, and the data on the accommodative power distribution, which is the difference between them are stored in the memory unit 55 together with a measurement date, examinee information (such as a name, an ID number, information indicating which side of the eye is to be measured and the like), measurement condition information (such as a set position of the fixation target), and the like. The examinee information is previously inputted using the keyboard 58, the mouse 57 and the like. The measurement date is obtained automatically by a clock included in the calculation and control unit 50. As the measurement condition information, conditions upon each measurement are stored.

Using the data stored as above, observation may be made on time-varying change (change after a period of time, or change observed at different time of a different day) in the accommodative power of one and the same eye to be examined. That is, based on the measurement date information, the examinee information, the measurement condition information and the like, the eye refractive power at far vision and at near vision are measured on the same eye under the same condition. Then, the previous data of that same eye is called up so that the calculation unit 52 compares the previously measured difference data, (the first difference data) with the difference data measured after a period of time (the second difference data) thereby to calculate the difference data (the third difference data). The thus obtained results are displayed in a manner similar to FIG. 6. Also, the third difference data may be displayed in the similar manner described above in terms of qualitative numeric data such as the maximum value, the minimum value, the average value, or the volume. Furnishing such results allows, for example, age-related change in accommodation of the crystalline lens to be known in detail, which provides a clue to figure out the mechanisms of decline of accommodative power. Alternatively, such information may be used to examine effectiveness of therapeutic drugs for preventing cataract from developing or therapeutic drugs for accommodative power recovery (or visual acuity recovery training).

In the embodiment described above, at near vision, the fixation target is placed at a certain distance arbitrarily. Yet, the fixation target may be moved to a point of the limit where accommodative power works. In the measurement consistent with this technique, after completing the measurement at far vision, the fixation target is gradually moved closer to the eye E by operating the switch 42. The examinee is instructed to gaze at the fixation target with the eye E and to respond when the fixation target blurs. At the time the response is given, the fixation target is stopped and the examinee is made to fixate the fixation target under this condition. This causes the eye E to be fully accommodated up to the limit. Here, by depressing the measurement switch to measure eye refractive power distribution at near vision, data on accommodative power distribution at the limit of accommodation is obtained. Further, a measurement is performed after a period of time in a similar manner in order to obtain the third difference data as described above. In this way, information about difference in the maximum accommodative power, which is obtained from the limit of the accommodative power, is provided in detail.

Further, eye refractive power measurement may be carried out using not only the phase difference method as above but also various other methods. One example is a method in which parallel light of a number of dot patterns is projected on the fundus of the eye and the light reflected from the fundus is received with a two-dimensional CCD (an area sensor). The refractive power distribution is obtained from the deviation of the detected dot pattern (this method is adopted in an apparatus so-called wave front analyzer). Alternatively, in another possible method, a parallel laser beam is made to enter the fundus of the eye, and a number of rays of light reflected from the fundus are photographed by a two-dimensional CCD via an array of a number of lenses in the photo-receiving system. The refractive power distribution is obtained from the deviation of the light on the two-dimensional CCD. Further, it is also possible to use a method in which parallel light such as a laser beam is made to enter the fundus of the eye while scanning the same with respect to the cornea of the eye. Then, the light reflected from the fundus is received with a quadrant photo-detector or an area sensor. The refractive power distribution is obtained from the deviation of the light received.

Further, in the embodiment disclosed above, the apparatus comprising the eye refractive power measurement optical system also calculates the accommodative power distribution. Yet, it is also applicable to perform calculation and display of the calculated results by a separate apparatus (an external computer or the like).

As has been described above, according to the present invention, eye refractive power distribution is measured with accommodative load applied to the eye being varied in order to find out about the change in accommodation of the eye in detail. The obtained results may be used, for example, in diagnosis of crystalline lens functions.

What is claimed is:

1. An ophthalmic apparatus comprising:
    an input unit with which data on eye refractive power distribution of an eye to be examined at far vision, which is an unaccommodated state of the eye, and data on eye refractive power distribution of the eye at near vision, which is an accommodated state of the eye are inputted;
    a display; and
    a calculation and control unit which obtains data on distribution of difference between both the inputted data on distribution, so as to display at least one of the following data on the display: the data on the eye refractive power distribution at far vision; the data on the eye refractive power distribution at near vision; and the obtained data on the distribution of difference.

2. The ophthalmic apparatus according to claim 1, further comprising an eye refractive power measurement unit which obtains data on eye refractive power distribution over each portion of a cornea of the eye, the eye refractive power measurement unit comprising:
    a projecting optical system for projecting a measurement target onto a fundus of the eye;
    a detecting optical system for detecting an image of the measurement target formed on the fundus; and
    a target presenting optical system for presenting a target to the eye at a variable distance, and
    wherein the input unit inputs the obtained data on the eye refractive power distribution to the calculation and control unit.

3. The ophthalmic apparatus according to claim 1, further comprising:
    a second input unit with which information about an examinee is inputted; and
    a memory unit which stores at least either the inputted data on the eye refractive power distribution at far vision and at near vision or the obtained data on the distribution of difference in association with the inputted information about the examinee, and
    wherein the calculation and control unit reads out the stored data based on the information about the examinee.

4. The ophthalmic apparatus according to claim 3, wherein the memory unit stores the data on the distribution of difference, and
    the calculation and control unit further obtains data on second distribution of difference between the read out data on the distribution of difference and newly obtained data on distribution of difference, so as to display at least one of the following data on the display: the read out data on the distribution of difference; the newly obtained data on the distribution of difference; and the data on the second distribution of difference.

5. The ophthalmic apparatus according to claim 1, wherein the calculation and control unit displays the data on the distribution in at least either color mapping display with a predetermined step of refractive power difference or three-dimensional display.

6. An ophthalmic apparatus comprising:

a projecting optical system for projecting a measurement target on a fundus of an eye to be examined;

a detecting optical system for detecting an image of the measurement target formed on the fundus;

a target presenting optical system for presenting a target to the eye at a variable distance;

a display; and a calculation and control unit which obtains data on eye refractive power distribution over each portion of a cornea of the eye based on results detected by the detecting optical system, and further obtains data on distribution of difference between the data on eye refractive power distribution that have been obtained with the target presented at different distances, so as to display at least the obtained data on the distribution of difference.

7. The ophthalmic apparatus according to claim 6, further comprising:

an input unit with which information about an examinee is inputted; and a memory unit which stores the obtained data on the distribution of difference in association with the inputted information about the examinee, and wherein the calculation and control unit reads out the stored data based on the information about the examinee.

8. The ophthalmic apparatus according to claim 7, wherein the calculation and control unit further obtains data on second distribution of difference between the read out data on the distribution of difference and newly obtained data on distribution of difference, so as to display at least one of the following data on the display: the read out data on the distribution of difference; the newly obtained data on the distribution of difference; and the data on the second distribution of difference.

9. The ophthalmic apparatus according to claim 6, wherein the calculation and control unit displays the data on the distribution in at least either color mapping display with a predetermined step of refractive power difference or three-dimensionnal display.

* * * * *